(12) United States Patent
Rafferty et al.

(10) Patent No.: US 9,451,364 B2
(45) Date of Patent: Sep. 20, 2016

(54) PRECONCENTRATING A SAMPLE IN A PRECONCENTRATOR EVACUATED TO SUBSTANTIALLY THE SAME PRESSURE AS AN ANALYTICAL DEVICE

(75) Inventors: David Rafferty, Webster, TX (US); James Wylde, Oak Leaf, TX (US); Michael Spencer, Manvel, TX (US); Pedro Ojeda, Pflugerville, TX (US)

(73) Assignee: 1ST DETECT CORPORATION, Austin, TX (US)

( * ) Notice: Subject to any disclaimer, the term of this patent is extended or adjusted under 35 U.S.C. 154(b) by 1090 days.

(21) Appl. No.: 13/392,739

(22) PCT Filed: Aug. 27, 2010

(86) PCT No.: PCT/US2010/047015
§ 371 (c)(1),
(2), (4) Date: Jul. 10, 2012

(87) PCT Pub. No.: WO2011/031559
PCT Pub. Date: Mar. 17, 2011

(65) Prior Publication Data
US 2012/0270334 A1    Oct. 25, 2012

Related U.S. Application Data

(60) Provisional application No. 61/237,457, filed on Aug. 27, 2009.

(51) Int. Cl.
*G01N 1/40* (2006.01)
*H04R 5/02* (2006.01)
(Continued)

(52) U.S. Cl.
CPC ............. *H04R 5/023* (2013.01); *A47C 7/72* (2013.01); *G01N 1/405* (2013.01); *G01N 27/622* (2013.01);
(Continued)

(58) Field of Classification Search
CPC .......... G01N 1/40; G01N 1/405; G01N 1/34; G01N 27/622; G01N 2030/008; G01N 2030/085; G01N 30/08; G01N 30/72; G01N 30/0011; G01N 30/0021; G01N 2033/0019; H01J 49/26; Y10T 436/255
See application file for complete search history.

(56) References Cited

U.S. PATENT DOCUMENTS 4,293,316 A    10/1981   Block
5,142,143 A *  8/1992   Fite et al. ............. 250/288
(Continued)

FOREIGN PATENT DOCUMENTS

| EP | 1396713 | 3/2004 |
| EP | 2045593 | 4/2009 |
| WO | 2007113486 | 10/2007 |
| WO | 2008021275 | 2/2008 |

OTHER PUBLICATIONS

Authorized Officer P. Groeneveld-Van Der Spek. International Search Report and Written Opinion in International Application No. PCT/US2010/047015, mailed Jan. 21, 2011, 14 pages.

(Continued)

*Primary Examiner* — Christopher A Hixson
(74) *Attorney, Agent, or Firm* — Finnegan, Henderson, Farabow, Garrett & Dunner, LLP

(57) ABSTRACT

A chemical analysis system is disclosed wherein, in evacuating a preconcentrator housing (2) prior to desorption, a pump system (13) reduces an internal pressure of the preconcentrator housing to a level substantially equal to an internal pressure of a chemical analyzer such that flow restrictors and/or membranes (15) between the chemical analyzer (7) and the preconcentrator housing (2) may be omitted. The chemical analysis system includes a chemical analyzer (7), a preconcentrator housing (2) coupled to the chemical analyzer, the preconcentrator housing enclosing a temperature control element (5, 18) and a sorbent material (1), the temperature control element configured to heat the sorbent material to adsorb or desorb a chemical of interest; and a pump system (13) coupled to the preconcentrator housing and the chemical analyzer, the pump system configured to evacuate the preconcentrator housing prior to desorption of the chemical of interest.

7 Claims, 15 Drawing Sheets

(51) Int. Cl.
    H01J 49/26      (2006.01)
    G01N 27/62      (2006.01)
    G01N 33/00      (2006.01)
    A47C 7/72       (2006.01)

(52) U.S. Cl.
    CPC .......... *G01N 33/0011* (2013.01); *H01J 49/26* (2013.01); *G01N 2033/0019* (2013.01); *H04R 2205/022* (2013.01); *Y10T 436/255* (2015.01)

(56) References Cited

U.S. PATENT DOCUMENTS

| | | | |
|---|---|---|---|
| 5,395,589 | A | 3/1995 | Nacson |
| 5,970,803 | A | 10/1999 | Staples et al. |
| 6,354,160 | B1 | 3/2002 | Staples et al. |
| 7,229,593 | B1 | 6/2007 | Ho |
| 2005/0109932 | A1* | 5/2005 | Mullock et al. ............ 250/288 |
| 2008/0311672 | A1 | 12/2008 | Dasgupta et al. |
| 2009/0090197 | A1* | 4/2009 | Finlay et al. ............ 73/863.12 |

OTHER PUBLICATIONS

Authorized Officer F. Bockstahl. International Preliminary Report on Patentability in International Application No. PCT/US2010/047015, mailed Dec. 2, 2011, 9 pages.

Bae et al., "A Fully-Integrated MEMS Preconcentrator for Rapid Gas Sampling," Air Force Technical Report AFRL-PR-WP-RP-2007-224, 2006, 6 pages.

Grate et al., "Smart Sensor System for Trace Organic Vapor Detection using a Temperature Controlled Array of Surface Acoustic Wave Vapor Sensors, Automated Pre-concentrator Tubes, and Pattern Recognition," Presented at the 183rd Electrochemical Society Meeting, 1993, 17 pages.

Ho et al., "Development of a Surface Acoustic Wave Sensor for In-Situ Monitoring of Volatile Organic Compounds," Sensors, 2003, 3:236-247.

Manoosingh, "Design of a Chemical Agent Detector Based on Polymer Coated Surface Acoustic Wave (SAW) Resonator Technology," PhD Dissertation, University of South Florida, Jun. 2004, 113 pages.

Thompson et al., "A coaxially heated membrane introduction mass spectrometry interface for the rapid and sensitive on-line measurement of volatile and semi-volatile organic contaminants in air and water at parts-per-trillion levels," Rapid Communications in Mass Spectrometry, 2006, 20(13):2000-2008.

Whitfield, "MEMS Based Resonant Senor Arrays: Selective Detection of Volatile and Toxic Chemicals," M. Eng. Dissertation, Massachusetts Institute of Technology, 2004, 59 pages.

Zee and Judy, MEMS Chemical Gas Sensor, Presented at 13th Biennial University/Government/Industry Microelectronics Symposium (UGIM '99), Jun. 1999, 3 pages.

* cited by examiner

Section A-A

PRECONCENTRATING A SAMPLE IN A PRECONCENTRATOR EVACUATED TO SUBSTANTIALLY THE SAME PRESSURE AS AN ANALYTICAL DEVICE

CROSS-REFERENCE TO RELATED APPLICATIONS

This application is the U.S. national stage application under 35 USC §371 of International Application Number PCT/US2010/047015 filed on Aug. 27, 2010, which claims the benefit of priority to U.S. Provisional Application Ser. No. 61/237,457, filed on Aug. 27, 2009, which is incorporated by reference herein.

TECHNICAL FIELD

This disclosure is related to the field of chemical analysis and detection, and more particularly to the use of a sample collection and introduction system that utilizes adsorption, desorption, and chamber evacuation techniques to increase the concentration of a sample introduced to a detection device such as a mass spectrometer.

BACKGROUND

Mass spectrometry is well recognized for use in chemical analysis due to the high resolution measurements that can be realized and because a mass spectrometer measures a fundamental property of chemicals that are introduced to the instrument. Other forms of chemical analysis instrumentation such as ion mobility spectrometers, surface acoustic wave devices, electrochemical cells, and similar instruments measure the constituents of a sample by inferring their presence from measurements of related phenomena such as resonant frequency changes, voltage changes, and drift time measurements.

Mass spectrometers operate at pressures well below that of these other instruments. Mass spectrometers typically operate at pressures of $10^{-6}$-$10^{-3}$ Torr, while other analytical instruments typically operate at approximately one atmosphere of pressure. It should be noted however, operating pressures for instruments that are different than those referenced here may be selected based on the specific design of a particular instrument without changing the nature of the implementations disclosed herein.

Because mass spectrometers operate at pressures well below that of atmospheric pressure, there will be fewer molecules present per unit volume in the instrument than for those instruments that operate at higher pressures. This is well described by the Ideal Gas Law:

pV=nRT where p is the pressure inside the analysis chamber of an instrument, V is the volume of the analysis chamber, n is the number of molecules present, R is a constant equal to 8.314 J mol$^{-1}$ K$^{-1}$, and T is the temperature of the sample.

For many applications, it is desirable to reduce the size of chemical analysis instruments. For example, it may be desirable for screeners in airports to carry an instrument through the facility that can detect the presence of explosives by analyzing the air around suspicious persons or objects and looking for traces of explosive material. Another example is that it may be desirable for first responders to carry an instrument to the scene of a fire or chemical emergency to gain foreknowledge of which chemicals are present. A further example is that it may be desirable for a health care professional to have a portable instrument that can be carried to a patient's bedside to analyze the patient's breath for chemicals that can indicate disease. It should be noted however that these examples are merely provided as illustration of the need for miniaturized instruments.

As mass spectrometers are decreased in size to that which enables easy portability, the volume of the instrument is decreased. Because mass spectrometers typically use lower operating pressure than other chemical analysis instruments, and as the mass spectrometer is decreased in size for ease of portability, the number of molecules present in the instrument during analysis is significantly reduced. This is illustrated by the Ideal Gas Law noted above by decreasing both p and V; as a result, the number of molecules present, n, is reduced accordingly.

The effect of reducing the detection volume of the instrument is to reduce the sensitivity of the instrument, where the sensitivity is the minimum external concentration of sample that can be measured by the instrument. For example, a mass spectrometer operating at $10^{-3}$ Torr, with an analysis chamber volume of 1 mm$^3$, operating at 25° C. will have 32.3×10$^9$ molecules present. A corresponding instrument that operates at atmospheric pressure (760 Torr) will have 24.6×10$^{15}$ molecules present. A corresponding instrument that operates at $10^{-3}$ Torr but has an analysis chamber that is 1 cm$^3$ will have 32×10$^{12}$ molecules present. Note that these calculations are provided to illustrate that miniaturizing instruments that operate at lowered pressured can have a significantly lower number of molecules available for analysis. Instruments that operate at other pressures and/or have analysis chambers of different volumes can be analyzed and similar calculations performed.

If a sample is introduced to a miniature mass spectrometer, the chance of detecting the presence of a chemical of interest present in that sample is thus significantly reduced. Typical field portable mass spectrometers are capable of detecting the presence of chemicals in an air sample introduced to the instrument down to approximately 1 ppm (parts per million). Techniques are available to those skilled in the art to improve the sensitivity of the instrument. For example, by coupling a mass spectrometer with a gas chromatograph, using special thermal desorption probes, and repeating the analysis multiple times. It should be noted that other examples exist and these are provided only for illustration purposes. The problem with the use of these techniques is that the time required to perform an analysis is significantly increased, typically from several seconds to several minutes; or in the case of a gas chromatograph coupled to a mass spectrometer, up to typically 30 minutes.

To be effective, portable instruments must be capable of detecting chemicals present at or below 1 ppb (parts per billion). For example, Table 1 shows the Immediate Danger to Life and Health (IDLH) values for several common Chemical Warfare Agents (CWAs) (adapted from Sun, Y. and Ong, K, Detection Technologies for Chemical Warfare Agents and Toxic Vapors, CRC Press, 2005).

As can be seen from examination of this table, some of the common agents are dangerous at concentrations down to 2 ppb; hence, instruments must be able to detect below this level.

TABLE 1

| CWA | CAS | IDLH (ppm) |
|---|---|---|
| GA | 71-86-6 | 0.030 |
| GB | 107-44-8 | 0.030 |

TABLE 1-continued

| CWA | CAS | IDLH (ppm) |
|---|---|---|
| GD | 96-64-0 | 0.008 |
| GF | 329-99-7 | 0.030 |
| VX | 50782-69-9 | 0.002 |

Also, for a mass spectrometer to be able to detect a chemical, it is introduced to the instrument in a gaseous form. Consider that many explosives have very low volatility indices and as such, emit a very low amount of vapor into the surrounding air.

As a result, for a portable instrument to be able to detect the presence of explosives simply by analyzing the air in the proximity of the instrument, it must be able to detect concentrations to extremely low levels, ideally parts per trillion (ppt).

To facilitate this low concentration detection, some systems include a chemical pre-concentrator to increase the apparent concentration of samples being introduced to the chemical analyzer. For example, the apparent concentration of a sample introduced into an analyzer can be increased by using a membrane between the sample inlet and the chemical analyzer to remove or block certain species, while allowing target species to flow into the analyzer. While membrane inlets have been proven effective in commercial applications, they are typically limited to small concentration gains (<100) and are selective in the types of materials that are allowed through the membrane. An alternative approach is to use solid sorbent tubes to trap the species of interest. Conventional sorbent tubes are typically composed of a metal or glass tube packed with glass fibers or beads coated with or comprised of absorptive material, solid absorbent (e.g., calcium chloride, silica gel), or a variety of sorbent materials suited for the particular application. It should be noted that the terms absorption (implying an interaction of the analyte with the bulk material) and adsorption (implying an interaction with the surface of a material) are both used interchangeably. The specific mechanism of collecting analyte is material dependant and all forms of collection are covered by the scope of this disclosure. The tubing is typically wrapped in Nichrome wire which heats the tubing when an electrical current is passed through it. During the collection phase, a sample is passed (e.g., by carrier gas, or liquid) through the tube while the sorbent material adsorbs the analyte. These sorbents are then heated, releasing the analyte into the analyzer in a much shorter time than they were absorbed, thus increasing the concentration "seen" by the chemical analyzer.

Indirectly heating the sorbent material often results in various inefficiencies. For example, the sorbent material typically provides poor heat conduction paths, thus hindering the heat flow to the interior of the sorbent material. Further, additional power and time is typically required to compensate for the loss of heat into the surroundings. Desorption time is also important from a performance point of view since the concentration gain is inversely proportional to the time required for desorption. In addition, the sorbent material often impedes the passage of the carrier gas during sampling and desorption. Still further, while large gains in concentration are possible, conventional assemblies may have other drawbacks, including, for example, 1) there can be a substantial amount of time and power required to adsorb & desorb sufficient material; 2) the various locations on the sorbent material are not heated simultaneously thus releasing the chemical at different times and hence, reducing the apparent concentration seen at any one sample time and broadening the overall resolution of the pre-concentrator; 3) reactions between the chemical, sorbent, and background matrix can skew measurements by introducing unknowns into the chemical analyzer; 4) the sorbent material is not heated uniformly thus the chemicals will be released at different times and to varying extents.

SUMMARY

In one general aspect, a chemical analysis system is disclosed wherein, in evacuating a preconcentrator housing prior to desorption, a pump system reduces an internal pressure of the preconcentrator housing to a level substantially equal to an internal pressure of a chemical analyzer such that flow restrictors and/or membranes between the chemical analyzer and the preconcentrator housing may be omitted. The chemical analysis system includes a chemical analyzer, a preconcentrator housing coupled to the chemical analyzer, the preconcentrator housing enclosing a temperature control element and a sorbent material, the temperature control element configured to heat the sorbent material to adsorb or desorb a chemical of interest; and a pump system coupled to the preconcentrator housing and the chemical analyzer, the pump system configured to evacuate the preconcentrator housing prior to desorption of the chemical of interest.

In another general aspect, preconcentration of a chemical sample is accomplished by providing a preconcentrator housing coupled to a chemical analyzer, the preconcentrator housing enclosing a temperature control element and a sorbent material, the temperature control element configured to heat the sorbent material to adsorb or desorb a chemical of interest, and a pump system coupled to the preconcentrator housing and the chemical analyzer, the pump system configured to evacuate the preconcentrator housing prior to desorption of the chemical of interest; evacuating the preconcentrator housing to reduce an internal pressure within the preconcentrator housing; and then, conducting current through the temperature control element to desorb the chemical of interest from the sorbent material into the evacuated preconcentrator housing; wherein, in evacuating the preconcentrator housing, an internal pressure of the preconcentrator housing is reduced to a level substantially equal to an internal pressure of the chemical analyzer.

In yet another general aspect, a chemical preconcentrator system having lower power requirements, increased sensitivity, and increased analysis speed is implemented using a temperature control element at least partially coated with sorbent material and wrapped around a tubular membrane in an essentially concentric manner to form an inlet assembly. The chemical preconcentrator system also includes: a chemical analyzer; a preconcentrator housing coupled to the chemical analyzer and enclosing the tubular membrane and the temperature control element at least partially coated with a sorbent material, the temperature control element configured to heat the tubular membrane and the sorbent material to desorb a chemical of interest during a desorption stage; and a pump system coupled to the preconcentrator housing and the chemical analyzer, the pump system configured to evacuate the preconcentrator housing prior to the desorption stage.

In another general aspect, preconcentration of a chemical sample is accomplished by providing a preconcentrator housing coupled to a chemical analyzer, the preconcentrator housing enclosing a tubular membrane and a temperature control element at least partially coated with a sorbent material, the temperature control element wrapped around the tubular membrane in an essentially concentric manner, and a pump system coupled to the preconcentrator housing and the chemical analyzer; evacuating, with the pump system, the preconcentrator housing to reduce an internal pressure within the preconcentrator housing; and then, desorbing a chemical of interest by conductively heating the tubular membrane and the sorbent material with the temperature control element.

In still another general aspect, a chemical preconcentrator system having lower power requirements, and improved sensitivity and analysis speed is implemented using a membrane that is operable in an absorbent mode and a desorptive/semi-permeable mode based on a temperature of the membrane and a setting of a temperature control element associated with the membrane. The chemical preconcentrator system includes a chemical analyzer; a preconcentrator housing coupled to the chemical analyzer, the preconcentrator housing enclosing the temperature control element and the membrane, the membrane having a lower rate of diffusion at lower temperatures than at higher temperatures, the temperature control element configured to heat the membrane to desorb a chemical of interest; and a pump system (13) coupled to the preconcentrator housing and the chemical analyzer, the pump system configured to evacuate the preconcentrator housing prior to desorption of the chemical of interest.

In another general aspect, preconcentration of a chemical sample is accomplished by providing a preconcentrator housing coupled to a chemical analyzer, the preconcentrator housing enclosing a temperature control element and a membrane having a lower rate of diffusion at lower temperatures than at higher temperatures, the temperature control element configured to heat the membrane to desorb a chemical of interest, and a pump system coupled to the preconcentrator housing and the chemical analyzer, the pump system configured to evacuate the preconcentrator housing prior to desorption of the chemical of interest; evacuating the preconcentrator housing to reduce an internal pressure within the preconcentrator housing; and then, adjusting a temperature setting of the temperature control element to transition the membrane from an absorbent mode to a desorptive/semi-permeable mode.

Disclosed herein are implementations of a chemical analyzer where the sorbent material and, if equipped, membrane are encased in essentially the same housing. Also, disclosed are techniques for operating the implementations where gases, for which analysis is undesirable that are occupying the housing containing the sorbent material and membrane, are largely evacuated prior to desorption. This evacuation step essentially eliminates the dead volume of the pre-concentrator housing, thus maximizing the concentration of the analyte.

Additionally, disclosed herein are techniques for improving the sensitivity of a portable mass spectrometer instrument by pre-concentrating the sample prior to introducing the sample to the analysis chamber. In an example, a pre-concentrator housing that contains a sorbent material, a heater, a temperature sensor, a valve, and fixtures appropriate for allowing a sample gas to flow through the pre-concentrator housing is situated near the inlet to the mass spectrometer analysis chamber to allow access between the pre-concentrator housing and the analysis chamber. In another example, a pre-concentrator housing is situated near the inlet to the mass spectrometer analysis chamber and contains a sorbent material, a heater, a temperature sensor, a membrane, and fixtures to allow the flow of a sample gas through the pre-concentrator housing. In implementations, methods and fixtures allow residual air to be removed from the pre-concentrator housing after a sufficient quantity of analyte has been absorbed by the sorbent material; the sorbent material (1) includes more than one sorbent material;

Some implementations may include one or more of the following features: a temperature sensor enclosed in the preconcentrator housing, the temperature sensor having a temperature sense terminal to communicate a sensed temperature; a temperature control unit coupled to the temperature control element and configured to supply a current to the temperature control element; a temperature sensor (3) enclosed in the preconcentrator housing (2), the temperature sensor having a temperature sense terminal (4) to communicate a sensed temperature; a temperature control unit (6, 19) coupled to the temperature control element (5, 18) and configured to supply a current to the temperature control element; the sorbent material (1) includes one or more of polyethylenimine (PEI), polyisobutylene (PIB), polyepichlorohydrin (PECH), carbon black, activated charcoal, fluoropolyol (FPOL), polyethylene maleate (PEM), polyvinyl propionate (PVPR), carbon nanotubes (CNTs), fullerenes, and/or polybiscyanopropyl-siloxane (SXCN); the temperature control element (18) is wrapped around the membrane (15) in an essentially concentric manner to form an inlet assembly (20); the membrane is formed in a tubular shape. Further, some implementations may include one or more of the following techniques: where conducting current through the temperature control element includes controllably increasing a temperature of the temperature control element to increase a desorption rate of the chemical of interest; sensing a temperature in the preconcentrator housing; conducting current through the temperature control element to adsorb the chemical of interest; where desorbing includes conducting current through the temperature control element to controllably increase a desorption rate of the chemical of interest; where the chemical of interest is a first chemical of interest, desorbing includes desorbing a second chemical of interest; where desorbing the second chemical of interest includes increasing a temperature of the temperature control element; readjusting the temperature setting of the temperature control element to increase a desorption rate of the chemical of interest; where the chemical of interest is a first chemical of interest, readjusting the temperature control element to increase a desorption rate of a second chemical of interest.

Particular embodiments of the subject matter described in this specification can be implemented so as to realize one or more of the following advantages. The pre-concentrator may exhibit a substantially higher concentration gain thus enabling significantly improved sensitivity for a wide variety of chemical detection instrumentation. The improvement in thermal efficiency means that the overall response time of the pre-concentrator is substantially improved allowing deployments in scenarios where fast response is desirable (e.g., airport explosives screening). Improved desorption through quick and even heating with reduced power consumption may be accomplished by applying a sorbent coating on the heating element. Measurement sensitivity may be improved by eliminating the need for a membrane between the desorption chamber and the analyzer. Further, eliminating the need for the membrane may improve detection of larger molecules such as explosives.

The details of one or more embodiments of the subject matter described in this specification are set forth in the accompanying drawings and the description below. Other features, aspects, and advantages of the subject matter will become apparent from the description, the drawings, and the claims.

BRIEF DESCRIPTION OF THE DRAWINGS

Like reference symbols in the various drawings indicate like elements.

DETAILED DESCRIPTION

In the description below, for the purposes of explanation, specific examples related to introducing an analyte into a mass spectrometer for analysis have been set forth in order to provide a thorough understanding of the implementations of the subject matter described in this specification. It is appreciated that the implementations described herein can be utilized in other capacities as well and need not be limited to mass spectrometers. For example, implementations may be used to improve the operation of other chemical analyzers, including, for example, gas and liquid chromatographs, ion mobility spectrometers, surface acoustic wave sensors, electrochemical cells, and optical spectrometers (e.g., Raman, UV-VIS, NIR, and similar chemical detectors). Accordingly, other implementations are within the scope of the claims.

Figure 1:
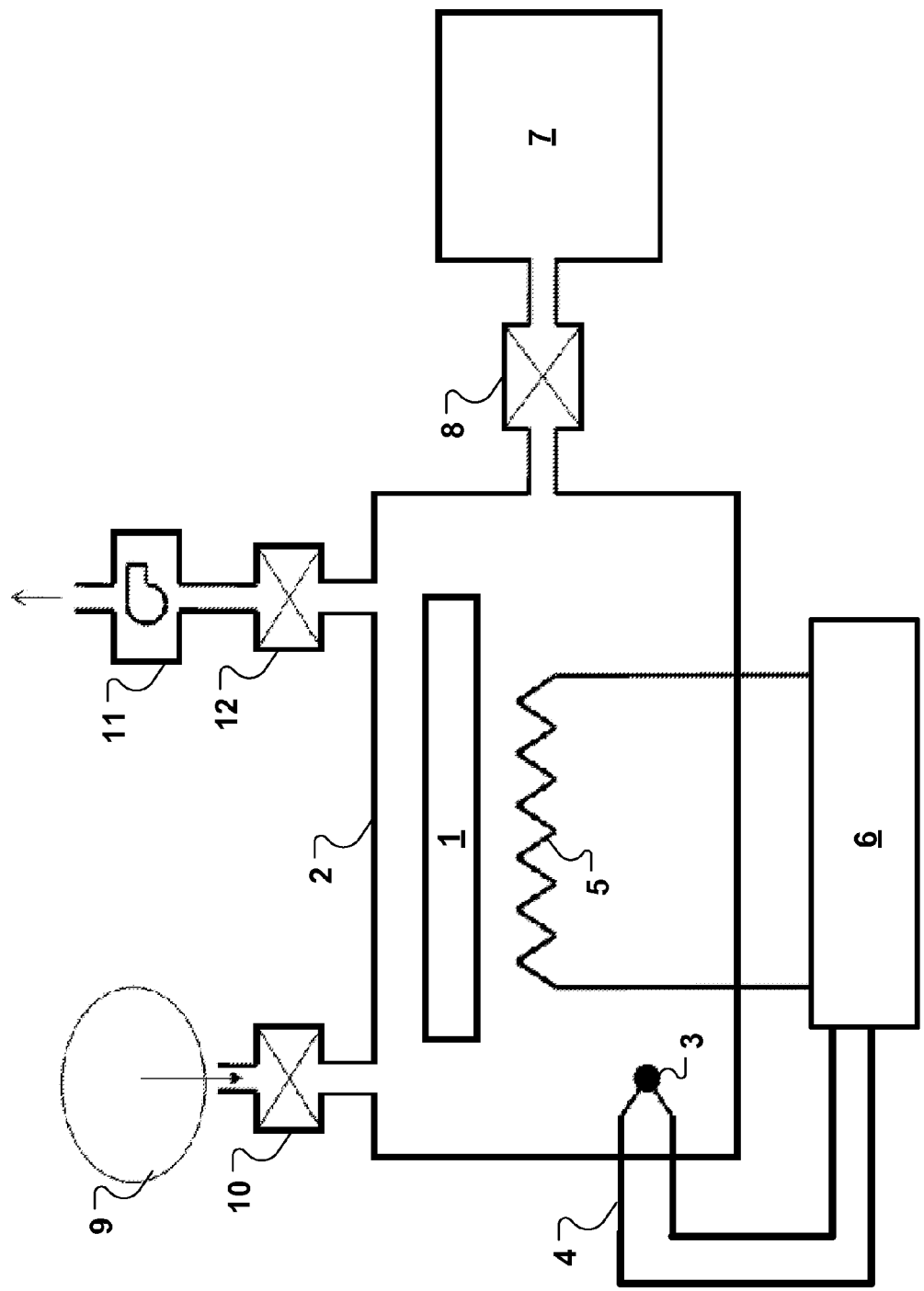
FIGS. 1-4, 8-10, and 13 illustrate system block diagrams of exemplary chemical analyzer systems.

FIG. 1 illustrates an exemplary analyzer system in which a sorbent material (1) is enclosed in a housing (2) that also contains a temperature sensor (3) with a temperature sense terminal (4) external to the housing (2). The housing (2) also contains a temperature control element (5) (e.g., a heating element) with a temperature control unit (6) for generating a current supplied to the temperature control element. In some implementations, the volume enclosed by the housing (2) is minimized. That is, the housing (2) is designed such that there is a minimum volume enclosing the components (e.g., sorbent, heater). Any volume beyond that which is needed reduces the pre-concentration gain, hence is undesirable. The housing (2) is connected to a mass spectrometer (7) through a port containing a valve (8). Other chemical analyzers may be used without changing the scope of this disclosure.

The sorbent material (1) may be comprised of a material that has the capability to store chemicals of interest and then release these chemicals with the application of an external control. The sorbent material (1) may be one or more of polyethylenimine (PEI), polyisobutylene (PIB), polyepichlorohydrin (PECH), carbon black, activated charcoal, fluoropolyol (FPOL), polyethylene maleate (PEM), polyvinyl propionate (PVPR), carbon nanotubes (CNTs), fullerenes, and/or polybiscyanopropyl-siloxane (SXCN). There are a significant number of references in the literature describing the sorption and desorption properties of materials. See, Zee, F and Judy, J., MEMS Chemical Gas Sensor, Presented at 13th Biennial University/Government/Industry Microelectronics Symposium (UGIM '99), June 1999; Manoosingh, L., Design of a Chemical Agent Detector Based on Polymer Coated Surface Acoustic Wave (SAW) Resonator Technology, PhD Dissertation, University of South Florida, June 2004; Ho, C. et. al., Development of a Surface Acoustic Wave Sensor for In-Situ Monitoring of Volatile Organic Compounds, Sensors 2003, vol. 3, pp. 236-247; Whitfield, G., MEMS Based Resonant Sensor Arrays: Selective Detection of Volatile and Toxic Chemicals, M. Eng. Dissertation, Massachusetts Institute of Technology, September 2004; Bae, B. et. al., A Fully-Integrated MEMS Preconcentrator For Rapid Gas Sampling, Air Force Technical Report AFRL-PR-WP-TP-2007-224, November 2006; and Grate, J. et. al., A Smart Sensor System for Trace Organic Vapor Detection using a Temperature Controlled Array of Surface Acoustic Wave Vapor Sensors, Automated Pre-concentrator Tubes, and Pattern Recognition, Presented at the 183rd Electrochemical Society Meeting, May 1993 (hereinafter, these references are referred to as "the above-noted references"). The work of Grate et al. is generally considered the seminal work. It should be noted that a different sorbent material or set of sorbent materials may be selected without changing the scope of this disclosure.

The chemicals of interest would be specified for a particular application, but may include chemical warfare agents (CWAs), toxic industrial chemicals (TICs), explosives, volatile organic compounds (VOCs), semi-volatile organic compounds (SVOCs), hydrocarbons, airborne contaminants, herbicides, and pesticides. It should be noted that many types and classes of chemicals exist and other chemicals may be specified without changing the scope of this disclosure.

In operation, a sample containing a chemical (9) that is desired to be detected by the mass spectrometer (7) is introduced through an inlet port containing a valve (10). The sample is drawn through the housing (2) by a sampling pump (11) that is connected to the housing (2) by a port containing a valve (12). Chemicals that are desired to be absorbed by the sorbent material (1) are stored by one or more of several mechanisms described in the above-noted references. The temperature control element (5) may be used to keep the sorbent material (1) at a specified temperature, which is measured with the temperature sensor (3) via the temperature sense terminal (4). When a sufficient amount of material is absorbed by the sorbent material (1), the inlet valve (10) is closed and the sampling pump (11) is used to remove gas from the housing (2). When the pressure in the housing (2) is reduced to a desired level, the output valve (12) is closed and the temperature control element (5) is adjusted to allow the sorbent material (1) to release the chemicals that have been absorbed. When the chemicals have been released from the sorbent material (1), the connection between the housing (2) and the mass spectrometer (7) is opened via the valve (8), and the released chemicals are introduced to the mass spectrometer (7) for analysis. Since the housing (2) was evacuated of substantially all of the gas contained therein prior to the release of the chemical from the sorbent material (1), the concentration of the chemical that is introduced to the mass spectrometer (7) is substantially increased over that of a chemical introduced from a non-evacuated housing.

For illustration, in one example, a housing (2) enclosing a volume of 1128 $mm^3$ has a sample stream (9) of air introduced at a flow rate of 1 l/min that contains 40 pg/l of tetracholoroethylene. After exposure to the sorbent material (1) for 7.57 seconds, and assuming that the sorbent material (1) stores 20% of the tetracholoroethylene passed over it, the sorbent material (1) will store 1.01 pg of tetracholorethylene. If the pressure in the housing (2) is not reduced from atmospheric pressure as described in the prior art, the resulting concentration of tetrachloroethylene in the remaining air will have a concentration of approximately 895 pg/l; thus, it will exhibit a pre-concentration gain of approximately 22. If the pressure in the housing (2) is reduced from atmospheric pressure to 1 Torr prior to the release of the tetrachloroethylene by the sorbent material (1), the tetracholoroethylene is released into substantially less air (1/760 in this example) and thus will exhibit a concentration gain of 17000. It is recognized that this example is provided for illustration purposes only, and the concentrations, exposure times, chemicals, pressures, volumes, and efficiencies may be different without changing the scope of this disclosure.

Figure 2:
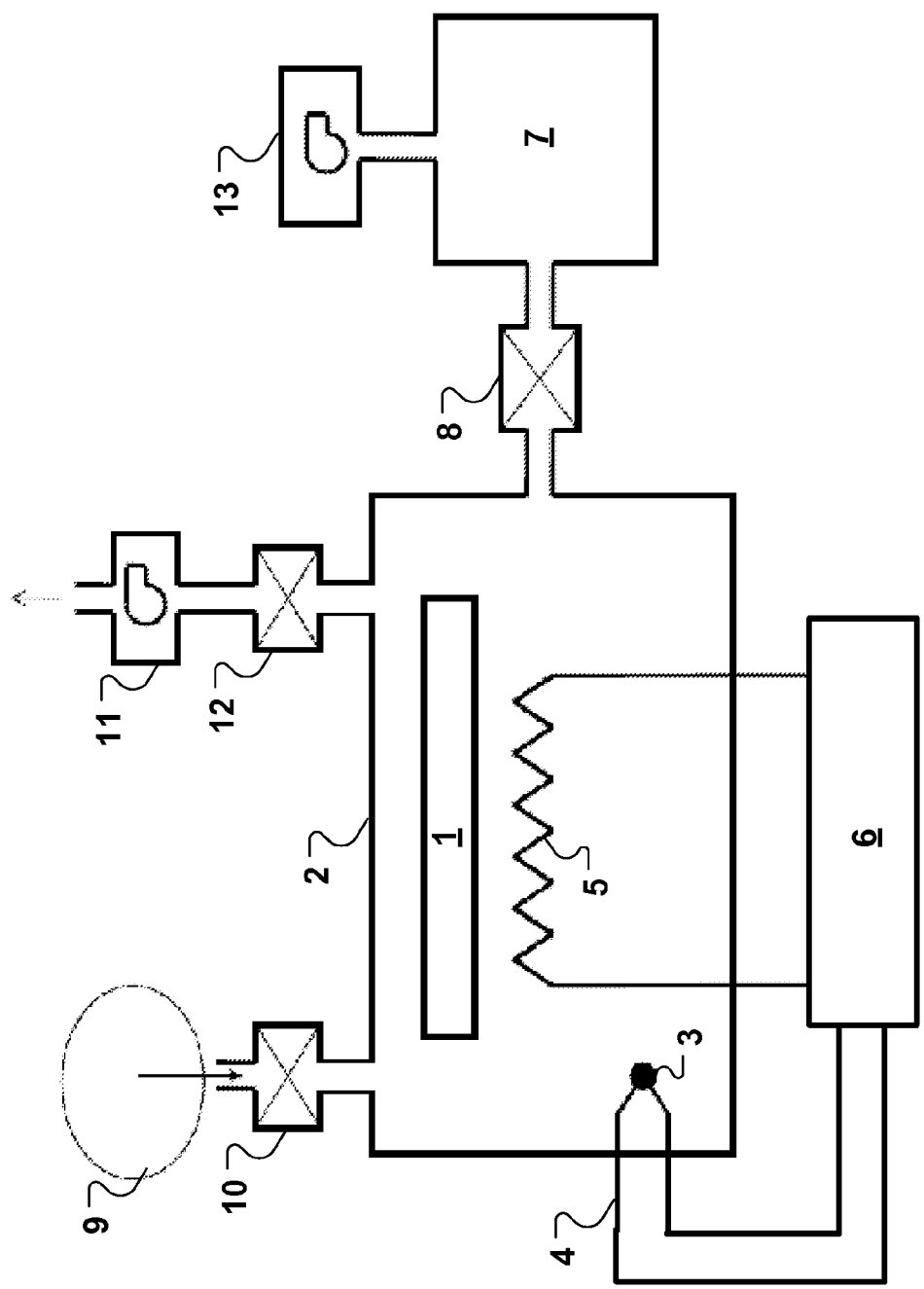

FIG. 2 illustrates an example in which a sorbent material (1) is enclosed in a housing (2) that also contains a temperature sensor (3) with a temperature sense terminal (4) external to the housing (2). The housing (2) also contains a temperature control element (5) with a temperature control unit (6) for generating a current supplied to the temperature control element. In some implementations, the volume enclosed by the housing (2) is minimized. The housing (2) is connected to a mass spectrometer (7) through a port containing a valve (8). Other chemical analyzers may be used without changing the scope of this disclosure.

In operation, a sample containing a chemical (9) that is desired to be detected by the mass spectrometer (7) is introduced through an inlet port containing a valve (10). The sample is drawn through the housing (2) by a sampling pump (11) that is connected to the housing (2) by a port containing a valve (12). Chemicals that are desired to be absorbed by the sorbent material (1) are stored by one or more of several mechanisms described in the above-noted references. The temperature control element (5) may be used to keep the sorbent material (1) at a specified temperature, which is measured with the temperature sensor (3) via the temperature sense terminal (4). When a sufficient amount of material is absorbed by the sorbent material (1), the inlet valve (10) and the outlet valve (12) are closed. The connection between the mass spectrometer (7) is opened via the valve (8), and the pumping system (13) associated with the mass spectrometer (7) is used to evacuate the housing (2) via the mass spectrometer (7) analysis chamber. When the pressure in the housing (2) is reduced to a desired level, the valve (8) is closed and the temperature control element (5) is adjusted to allow the sorbent material (1) to release the chemicals that have been absorbed. Note that valve (8) could be left open if the desorption is sufficiently fast. When the chemicals have been released from the sorbent material (1), the connection between the housing (2) and the mass spectrometer (7) is opened via the valve (8) and the released chemical introduced to the mass spectrometer (7) for analysis. Since the housing (2) was evacuated of substantially all of the gas contained therein prior to the release of the chemical from the sorbent material (1), the concentration of the chemical that is introduced to the mass spectrometer (7) is substantially increased over that of a chemical introduced from a non-evacuated housing.

Figure 3:
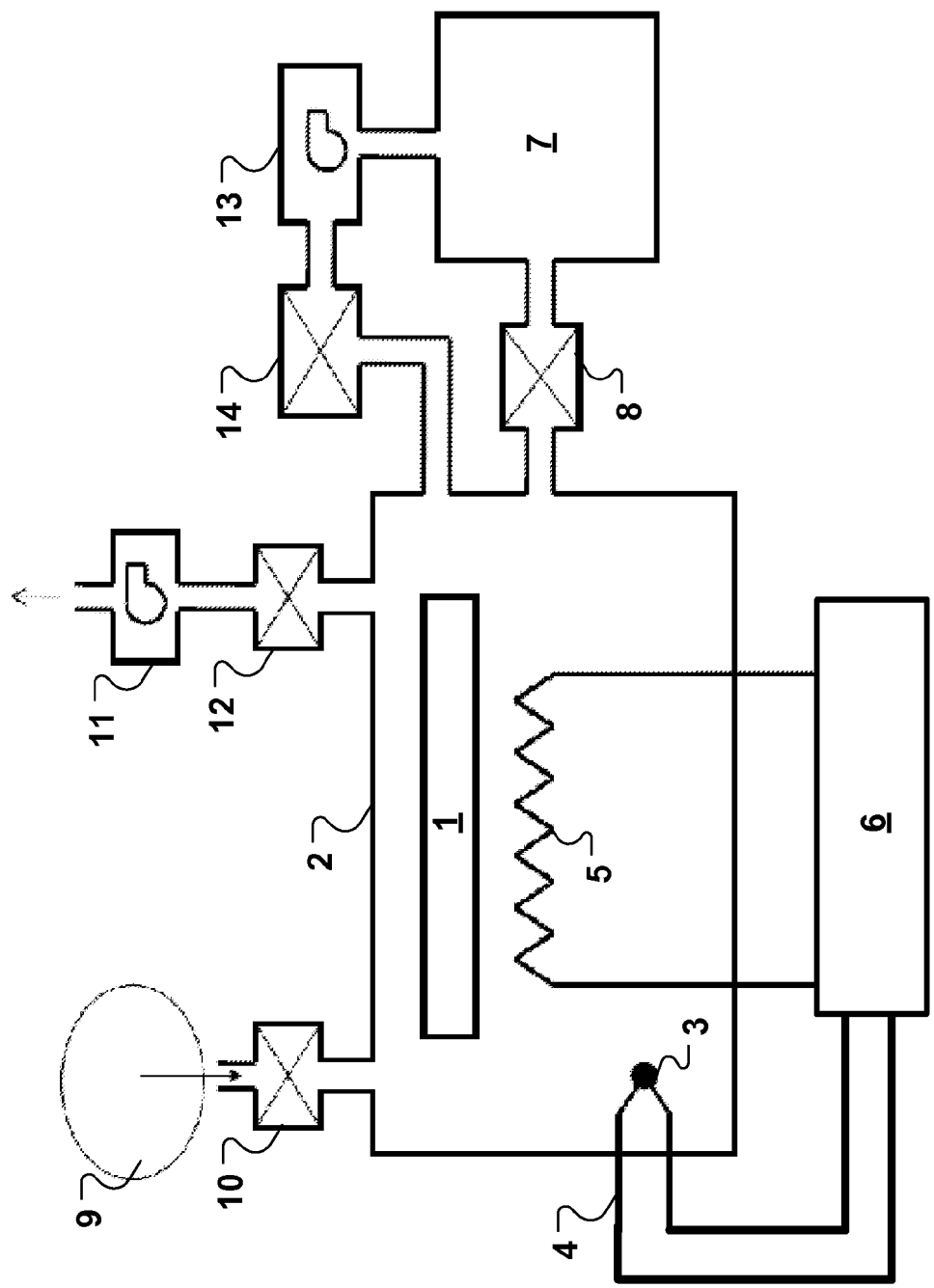

FIG. 3 illustrates an implementation in which a sorbent material (1) is enclosed in a housing (2) that also contains a temperature sensor (3) with a temperature sense terminal (4) external to the housing (2). The housing (2) also contains a temperature control element (5) with a temperature control unit (6) for generating a current supplied to the temperature control element. In some implementations, the volume enclosed by the housing (2) is minimized. The housing (2) is connected to a mass spectrometer (7) through a port containing a valve (8). The housing (2) is also connected to a pumping system (13) that is also connected to the mass spectrometer (7). Examples of the pumping system (13) include turbo and roughing pumps, getter pumps, ion pumps, and scroll cage pumps. It should be noted that a different type of chemical analyzer (7) or a different type of pump (13) may be selected without changing the scope of this disclosure. It should also be noted that the housing (2) may be connected to the pump (13) or combination of pumps through various means such as directly to the turbo pump, directly to the roughing pump, or other mechanism without changing the scope of this disclosure. It should also be noted that the housing (2) may be connected to external pumps that are not connected to the mass spectrometer (7) without changing the scope of this disclosure.

In operation, a sample containing a chemical (9) that is desired to be detected by the mass spectrometer (7) is introduced through an inlet port containing a valve (10). The sample is drawn through the housing (2) by a sampling pump (11) that is connected to the housing (2) by a port containing a valve (12). Chemicals that are desired to be absorbed by the sorbent material (1) are stored by one or more of several mechanisms described in the above-noted references. The temperature control element (5) may be used to keep the sorbent material (1) at a specified temperature, which is measured with the temperature sensor (3) via the temperature sense terminal (4). When a sufficient amount of material is absorbed by the sorbent material (1), the inlet valve (10) and the outlet valve (12) are closed. The housing (2) is then evacuated by opening the valve (14) and evacuating substantially all of the gas in the housing (2) via the pumping system (13). When the pressure in the housing (2) is reduced to a desired level, the valve (14) is closed and the temperature control element (5) is adjusted to allow the sorbent material (1) to release the chemicals that have been absorbed. When the chemicals have been released from the sorbent material (1), the connection between the housing (2) and the mass spectrometer (7) is opened via the valve (8) and the released chemical introduced to the mass spectrometer (7) for analysis. Since the housing (2) was evacuated of substantially all of the gas contained therein prior to the release of the chemical from the sorbent material (1), the concentration of the chemical that is introduced to the mass spectrometer (7) is substantially increased over that of a chemical introduced from a non-evacuated housing.

Some implementations may optionally include a flow control device, such as, for example, a flow restrictor, a pressure barrier, or a barrier membrane (such as those described below with respect to other implementations), between housing (2) and the mass spectrometer (7) to restrict the flow of the chemical released from sorbent material (1) into the chemical analyzer during desorption. In general, however, the flow control device can be omitted by reducing housing (2) to the same pressure as the chemical analyzer chamber and by utilizing the drag in pumping system (13) coupled to mass spectrometer (7) to introduce the released chemical into the chemical analyzer. Such implementations eliminate the need for reduced pressure transport gases and/or for forming an intermediate pressure region within the housing (2), for example, through the use of a separate pump to create a pressure differential for transport. Further, by eliminating the need for a flow restrictor or barrier membrane, measurement sensitivity may be improved for certain chemicals due to increased concentrations of the released sample reaching the mass spectrometer (7), for example, due to the longer mean free paths. Correspondingly, by eliminating the membrane or other restrictors, a broader range of chemicals can be analyzed, including, for example, those having larger molecular structures whose concentrations would have been diminished or blocked by the membrane. In particular applications, however, increased sensitivity for a more narrow range of chemicals may be accomplished by using a membrane to allow only chemicals of interest to pass. Thus, in some implementations, concentrations, and therefore, detection sensitivity, of certain chemicals may be improved by using a membrane as described in more detail below.

Figure 4:
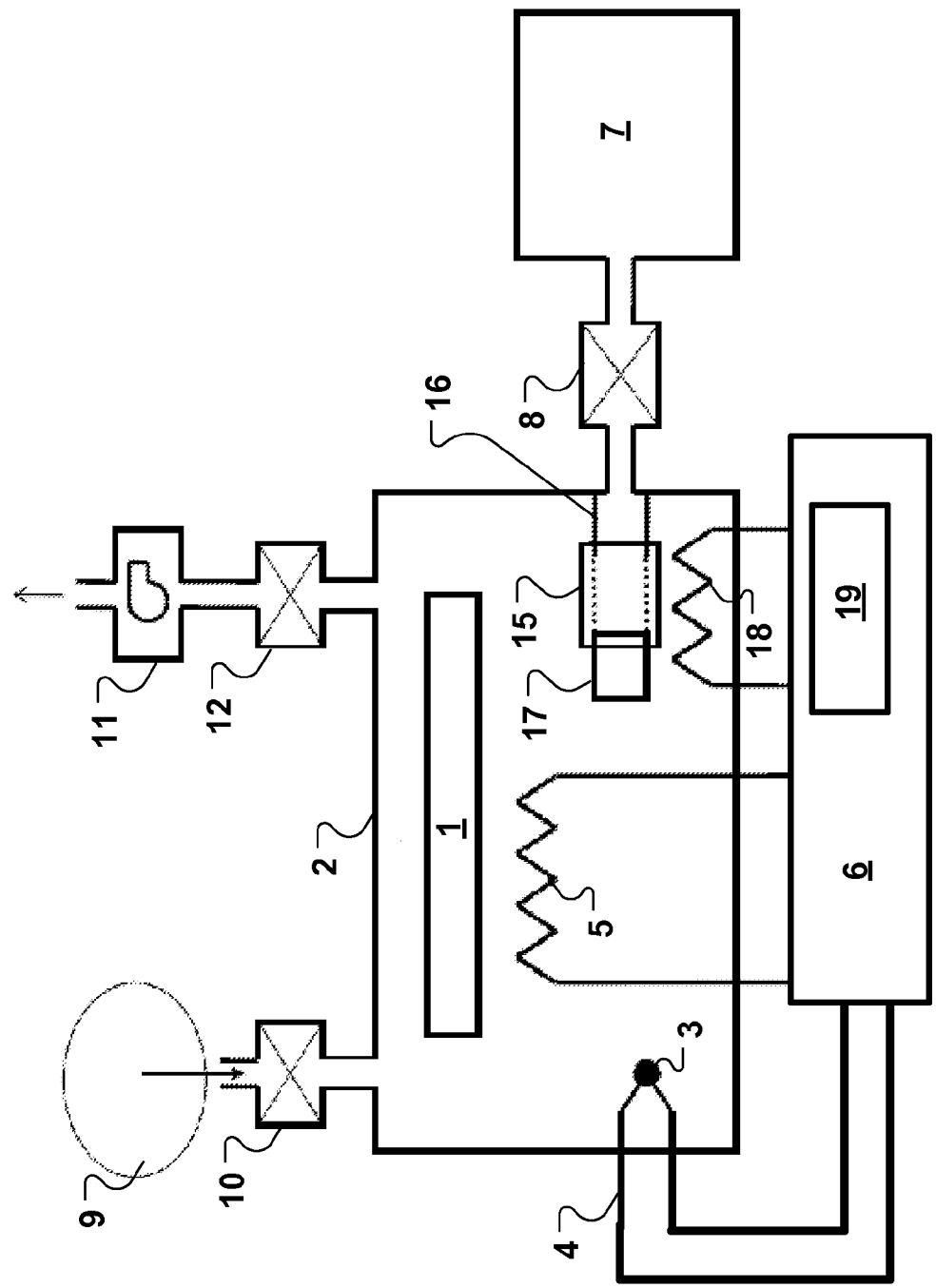
Figure 5:
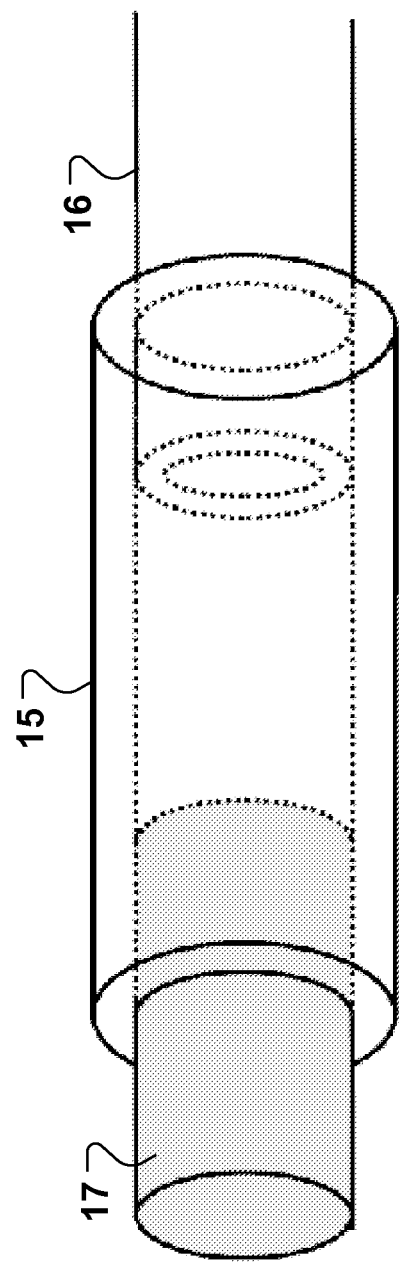
FIG. 5 is a perspective view of a cylindrical membrane.

FIG. 4 illustrates an example in which a sorbent material (1) is enclosed in a housing (2) that also contains a temperature sensor (3) with a temperature sense terminal (4) external to the housing (2). The housing (2) also contains a temperature control element (5) with a temperature control unit (6) for generating a current supplied to the temperature control element. In some implementations, the volume enclosed by the housing (2) is minimized. The housing (2) is connected to the mass spectrometer (7) through a port containing a valve (8) and membrane (15). As illustrated in FIG. 5, the membrane (15) may be cylindrical in nature and connected to the housing (2) via a tube (16) and closed with a plug (17).

Figure 6:
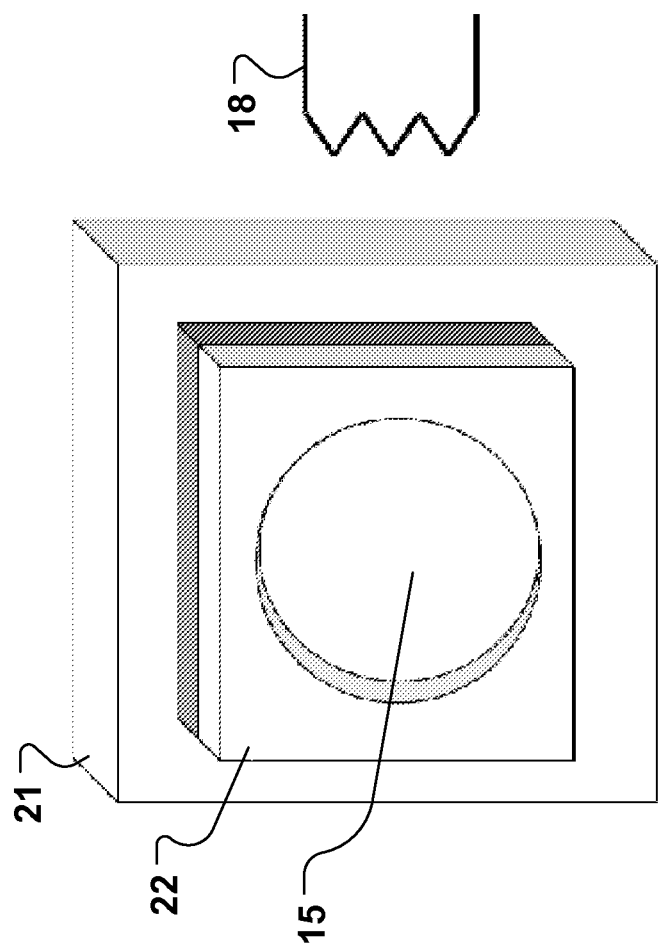
FIG. 6 is a perspective view of a diaphragm shaped membrane.
Figure 7:
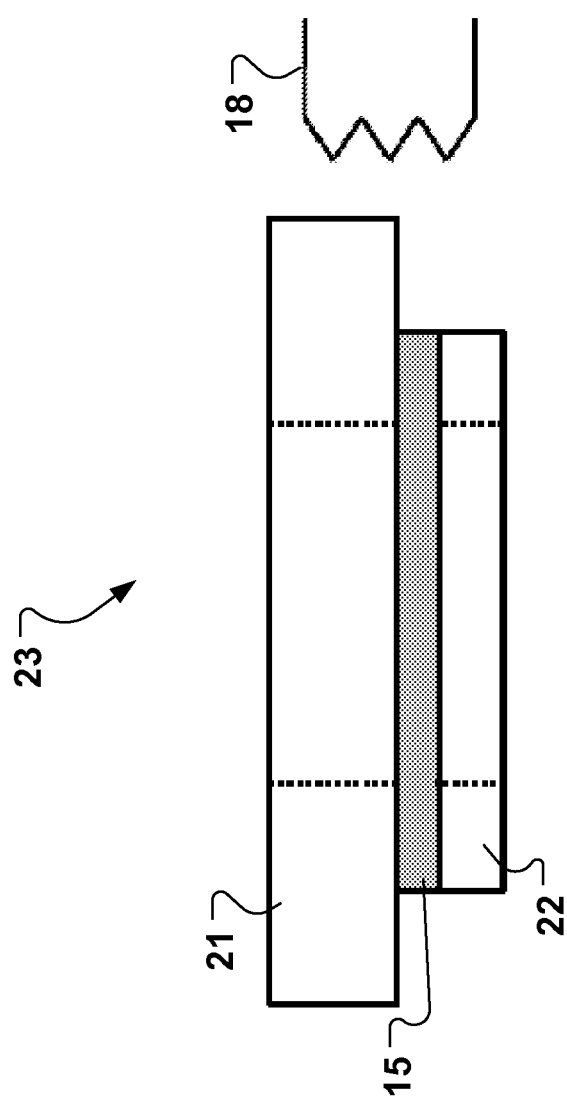
FIG. 7 is a top view of a diaphragm shaped membrane.
Figure 8:
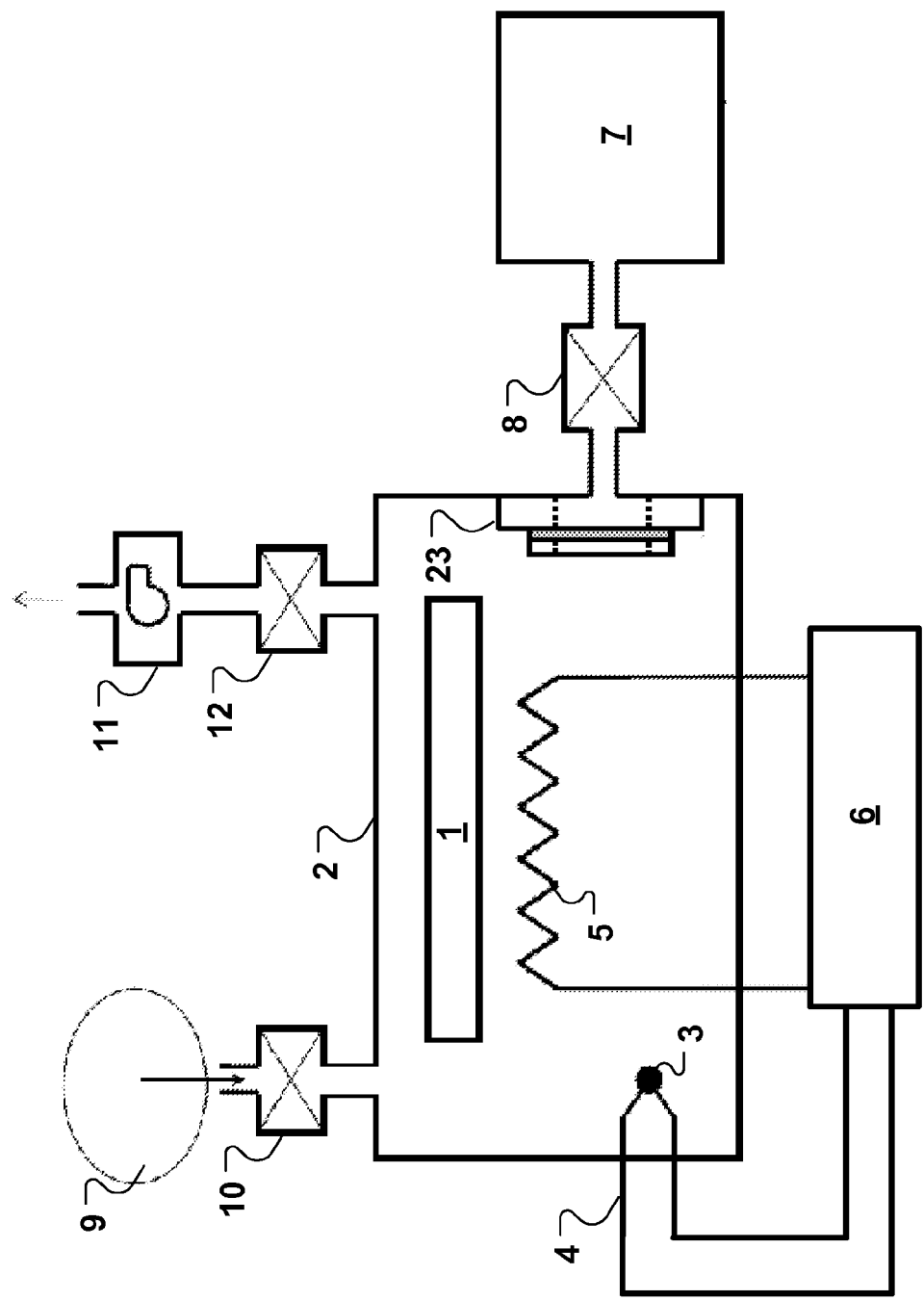

In some implementations, the membrane (15) is diaphragm shaped as illustrated in FIGS. 6 and 7. The membrane (15) is attached to a mount (21) containing an orifice, which, in some implementations, is heated by a heater (18) and held in place by a member (22) containing an orifice. In this example, the diaphragm assembly (23) is placed in the pre-concentrator housing (2) such that it forms a barrier between the pre-concentrator housing (2) and the mass spectrometer (7) as illustrated in FIG. 8. Membrane (15) may be configured in other ways. The membrane (15) is chosen to allow chemicals of interest to pass through the membrane (15) and to not allow the passage of chemicals for which it is not desired to introduce to the mass spectrometer (7). The membrane (15) may be formed of a polymeric material, such as polydimethylsiloxane (PDMS). It should be noted that a different type of chemical analyzer (7) or membrane material (15) can be used without changing the scope of this disclosure. In this example, a second temperature control element (18) with its own temperature control unit (19) may optionally be included.

In operation, a sample containing a chemical (9) that is desired to be detected by the mass spectrometer (7) is introduced through an inlet port containing a valve (10). The sample is drawn through the housing (2) by a sampling pump (11) that is connected to the housing (2) by a port containing a valve (12). Chemicals that are desired to be absorbed by the sorbent material (1) are stored by one or more of several mechanisms described in the above-noted references. The temperature control element (5) may be used to keep the sorbent material (1) at a specified temperature, which is measured with the temperature sensor (3) via the temperature sense terminal (4). When a sufficient amount of material is absorbed by the sorbent material (1), the inlet valve (10) is closed and the sampling pump (11) is used to remove gas from the housing (2). When the pressure in the housing (2) is reduced to a desired level, the output valve (12) is closed, and the temperature control element (5) is adjusted to allow the sorbent material (1) to release the chemicals that have been absorbed. When the chemicals have been released from the sorbent material (1), the connection between the housing (2) and the mass spectrometer (7) is opened via the valve (8), the temperature of the membrane (15) is adjusted to allow diffusion via the temperature control element (18), and the released chemical introduced to the mass spectrometer (7) for analysis via the membrane (15). Since the housing (2) was evacuated of substantially all of the gas contained therein prior to the release of the chemical from the sorbent material (1), the concentration of the chemical that is introduced to the mass spectrometer (7) is substantially increased over that of a chemical introduced from a non-evacuated housing. Since the membrane (15) further removes undesirable chemicals from the matrix, the concentration is further enhanced. In some implementations, valve (8) is omitted if the membrane material (15) prevents a majority of the sample (9) material from passing into the vacuum chamber (7) when the temperature of the membrane (15) is adjusted to operate such that the rate of diffusion is minimal.

Figure 9:
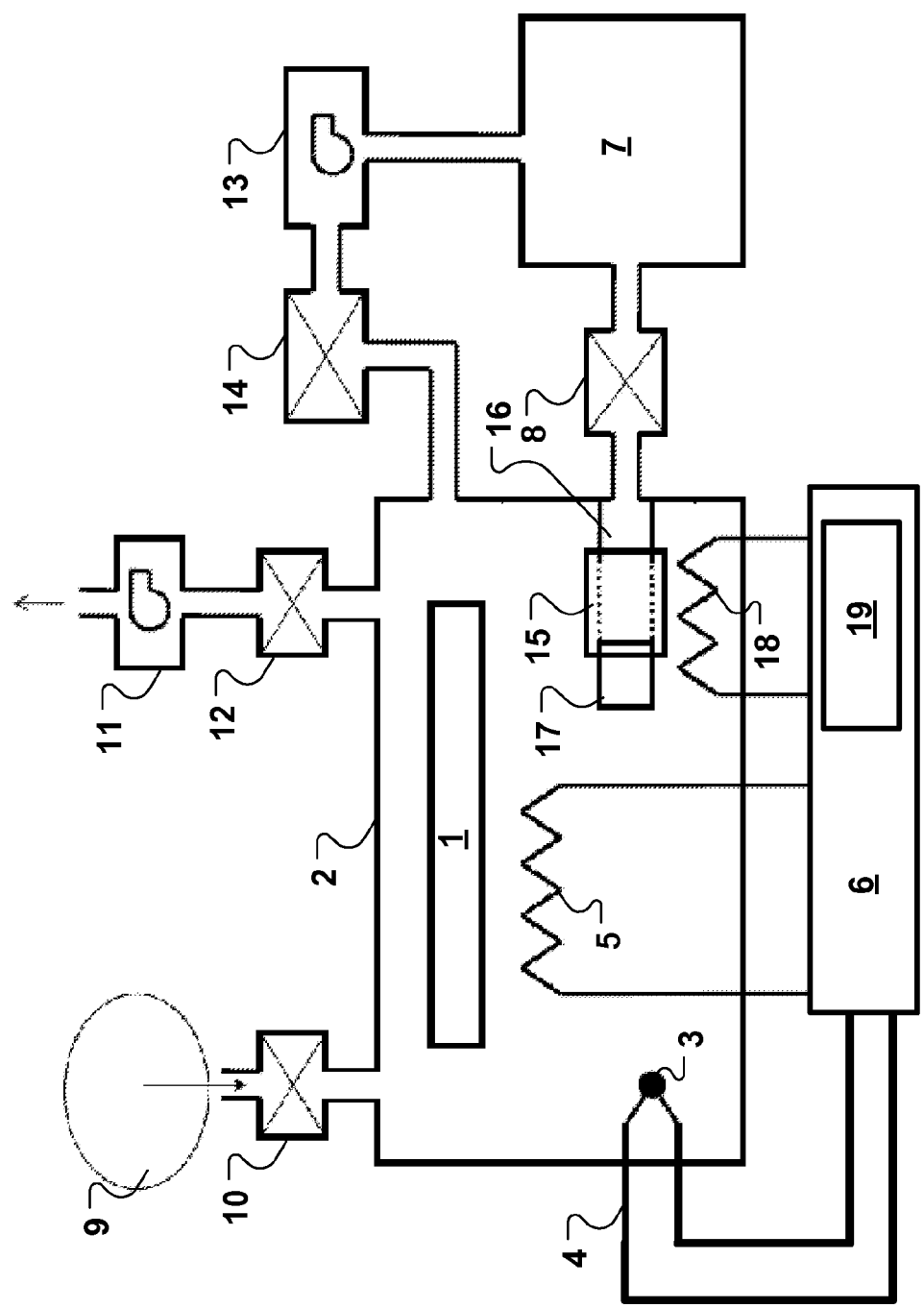

FIG. 9 illustrates an implementation in which a sorbent material (1) is enclosed in a housing (2) that also contains a temperature sensor (3) with a temperature sense terminal (4) external to the housing (2). The housing (2) also contains a temperature control element (5) with a temperature control unit (6) for generating a current supplied to the temperature control element. In some implementations, the volume enclosed by the housing (2) is minimized. The housing (2) is connected to the mass spectrometer (7) through a port containing a valve (8) and a membrane (15). The membrane (15) may be cylindrical in nature and connected to the housing (2) via a tube (16) and closed with a plug or cap (17) (see FIG. 5). The membrane (15) is chosen to allow chemicals of interest to pass through the membrane (15) and to not allow the passage of chemicals for which it is not desired to introduce to the mass spectrometer (7). The membrane (15) may be formed of a polymeric material, such as polydimethylsiloxane (PDMS). The housing (2) is also connected to a pumping system (13) that is also connected to the mass spectrometer (7). Examples of the pumping system (13) include turbo and roughing pumps, getter pumps, ion pumps, and scroll cage pumps. A different type of chemical analyzer (7) or a different type of pump (14) may be used without changing the scope of this disclosure. In this example, a second temperature control element (18) with its own temperature control unit (19) may optionally be included. In some implementations, the housing (2) is connected to external pumps that are not connected to the mass spectrometer (7).

In operation, a sample containing a chemical (9) that is desired to be detected by the mass spectrometer (7) is introduced through an inlet port containing a valve (10). The sample is drawn through the housing (2) by a sampling pump (11) that is connected to the housing (2) by a port containing a valve (12). Chemicals that are desired to be absorbed by the sorbent material (1) are stored by one or more of several mechanisms described in the above-noted references. The temperature control element (5) may be used to keep the sorbent material (1) at a specified temperature, which is measured with the temperature sensor (3) via the temperature sense terminal (4). When a sufficient amount of material is absorbed by the sorbent material (1), the inlet valve (10) and the outlet valve (12) are closed. The housing (2) is then evacuated by opening the valve (14) and evacuating substantially all of the gas in housing (2) via the pumping system (13). When the pressure in the housing (2) is reduced to a desired level, the valve (14) is closed and the temperature control element (5) is adjusted to allow the sorbent material (1) to release the chemicals that have been absorbed. When the chemicals have been released from the sorbent material (1), the connection between the housing (2) and the mass spectrometer (7) is opened via the valve (8), the temperature of the membrane (15) is adjusted to allow diffusion via temperature control element (18), and the released chemical introduced to the mass spectrometer (7) for analysis via the membrane (15). Since the housing (2) was evacuated of substantially all of the gas contained therein prior to the release of the chemical from the sorbent material (1), the concentration of the chemical that is introduced to the mass spectrometer (7) is substantially increased over that of a chemical introduced from a non-evacuated housing. Since the membrane (15) further removes undesirable chemicals from the matrix, the concentration is further enhanced.

In some implementations, valve (8) is omitted if the membrane material (15) prevents a majority of the sample (9) material from passing into the vacuum chamber (7) when the temperature of the membrane (15) is adjusted to operate such that the rate of diffusion is minimal.

Figure 10:
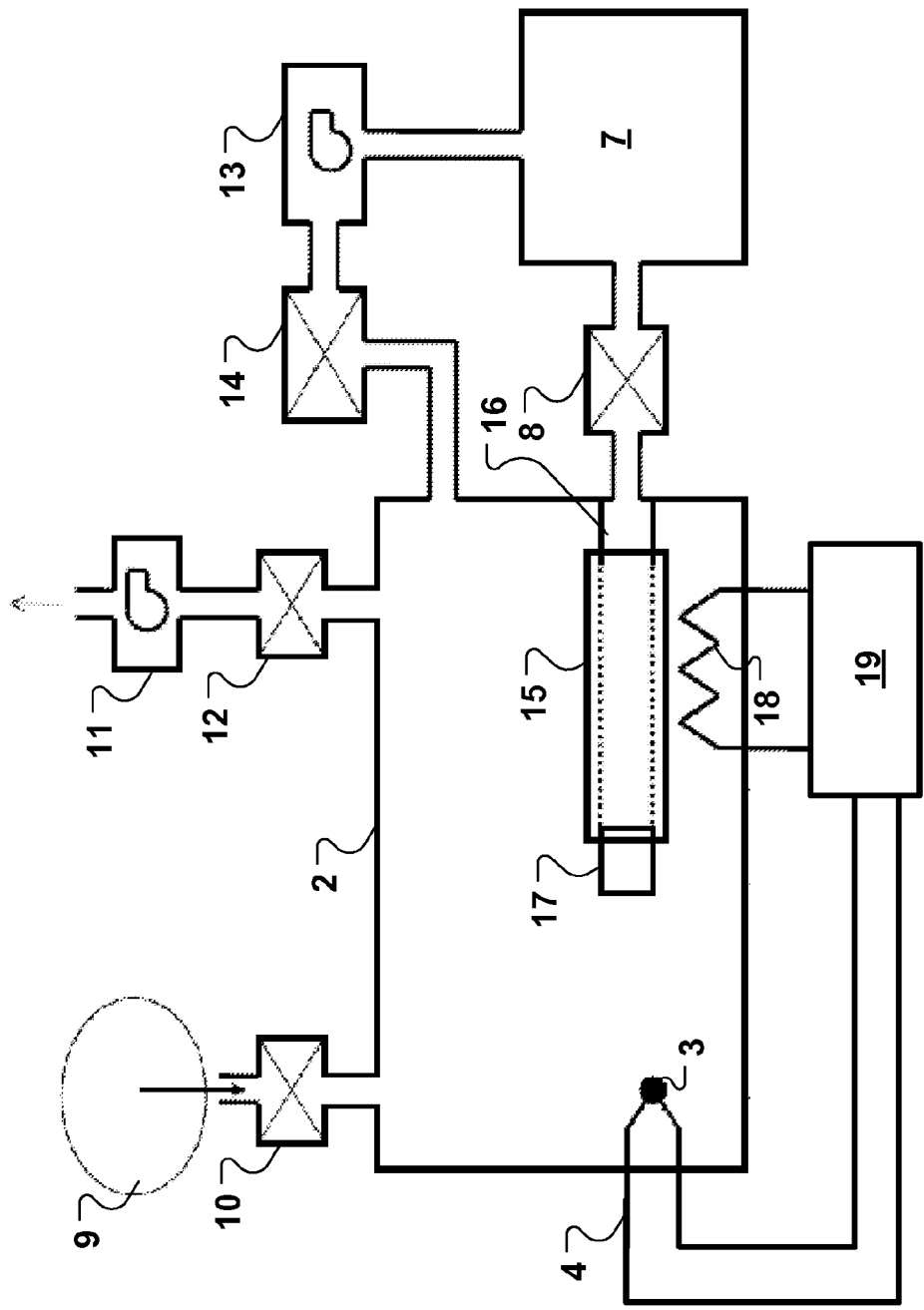

FIG. 10 illustrates an example in which a membrane (15) is enclosed in a housing (2) that also contains a temperature sensor (3) with a temperature sense terminal (4) external to the housing (2). The housing (2) also contains a temperature control element (18) with a temperature control unit (19) for generating a current supplied to the temperature control element. In some implementations, the volume enclosed by the housing (2) is minimized. The housing (2) is connected to the mass spectrometer (7) through a port containing a valve (8) and the membrane (15). The membrane (15) may be cylindrical in nature and connected to the housing (2) via a tube (16) and closed with a plug (17). The membrane (15) is chosen and configured such that it will act as a sorbent material at a certain temperature and a desorber and a semi-permeable membrane at another temperature. The housing (2) is also connected to a pumping system (13) that is also connected to the mass spectrometer (7). Examples of pumping system (13) include turbo and roughing pumps, getter pumps, ion pumps, and scroll cage pumps. A different type of chemical analyzer (7) or a different type of pump (14) may be used without changing the scope of this disclosure.

In operation, a sample containing a chemical (9) that is desired to be detected by the mass spectrometer (7) is introduced through an inlet port containing a valve (10). The sample is drawn through the housing (2) by a sampling pump (11) that is connected to the housing (2) by a port containing a valve (12). Chemicals that are desired to be absorbed by the membrane (15) are stored by one or more of several mechanisms described in the above-noted references. The temperature control element (18) may be used to keep the sorbent material (1) at the specified temperature, which is measured with the temperature sensor (3) via the temperature sense terminal (4), such that the sorbent material (1) operates in a mode where the rate of absorption is substantially greater than the rate of desorption. When a sufficient amount of material is absorbed by the sorbent material (1), the inlet valve (10) and the outlet valve (12) are closed. The housing (2) is then evacuated by opening the valve (14) and evacuating substantially all of the gas in the housing (2) via the pumping system (13). When the pressure in the housing (2) is reduced to a desired level, the valve (14) is closed, and the temperature control element (18) is adjusted to alter a mode of operation of the sorbent material (1) such that the rate of desorption is substantially greater than the rate of absorption. The connection between the housing (2) and the mass spectrometer (7) is opened via the valve (8) and the released chemical introduced to the mass spectrometer (7) for analysis. Since the housing (2) was evacuated of substantially all of the gas contained therein prior to the release of the chemical from the sorbent material (1), the concentration of chemical that is introduced to the mass spectrometer (7) is substantially increased over that of a chemical introduced from a non-evacuated housing.

In some implementations, valve (8) is omitted if the membrane material (15) prevents a majority of the sample (9) material from passing into the vacuum chamber (7) when the temperature of the membrane (15) is adjusted to operate such that the rate of diffusion is minimal. The alternative techniques for evacuating the housing (2) described with respect to FIGS. 1-3 may be utilized in without changing the scope of this disclosure.

Referring again to FIG. 9, in some implementations, the membrane (15) is chosen and configured such that it will act as a sorbent material at a certain temperature and a desorber and a semi-permeable membrane at another temperature. Further, the sorbent material (1) is chosen such that the chemical storage capacity of the material is greater at lower temperatures than at higher temperatures.

In operation, a sample containing a chemical (9) that is desired to be detected by the mass spectrometer (7) is introduced through an inlet port containing a valve (10). The sample is drawn through the housing (2) by a sampling pump (11) that is connected to the housing (2) by a port containing a valve (12). Chemicals that are desired to be absorbed by the sorbent material (1) are stored by one or more of several mechanisms described in the above-noted references. The temperature control element (5) may be used to keep the sorbent material (1) at a specified temperature, which is measured with the temperature sensor (3) via the temperature sense terminal (4), such that the sorbent material (1) operates in a mode where the rate of absorption is substantially greater than the rate of desorption. The temperature control element (18) may be used to control the temperature of the membrane (15) such that the membrane material will absorb the chemicals using a mechanism similar to the sorbent material (1). The membrane (15) and operating temperature are chosen such that the chemical will be absorbed but the rate of diffusion across the membrane (15) is essentially minimal. When a sufficient amount of material is absorbed by the sorbent material (1) and the membrane (15), the inlet valve (10) and the outlet valve (12) are closed. The housing (2) is then evacuated by opening the valve (14) and evacuating substantially all of the gas in the housing (2) via the pumping system (13). When the pressure in the housing (2) is reduced to a desired level, the valve (14) is closed, and the temperature control element (5) is adjusted to alter a mode of operation of the sorbent material (1) such that the rate of desorption is substantially greater than the rate of absorption. The temperature of the membrane (15) is also controlled by temperature control element (18) such that the rate of desorption is substantially higher than the rate of absorption, and the rate of diffusion across the membrane (15) is substantially increased. When the chemicals have been released from the sorbent material (1), the connection between the housing (2) and the mass spectrometer (7) is opened via the valve (8) and the released chemical introduced to the mass spectrometer (7) for analysis. Since the housing (2) was evacuated of substantially all of the gas contained therein prior to the release of the chemical from the sorbent material (1), the concentration of the chemical that is introduced to the mass spectrometer (7) is substantially increased over that of a chemical from a non-evacuated housing.

Valve (8) may be omitted if the membrane material (15) prevents a majority of the sample (9) material from passing into the vacuum chamber (7) when the temperature of the membrane (15) is adjusted to operate such that the rate of diffusion is minimal. Further, some examples include a single temperature control element and temperature control unit to control the rate of diffusion, rate of desorption, and adsorption of the membrane (15) and sorbent material (1).

Figure 11:
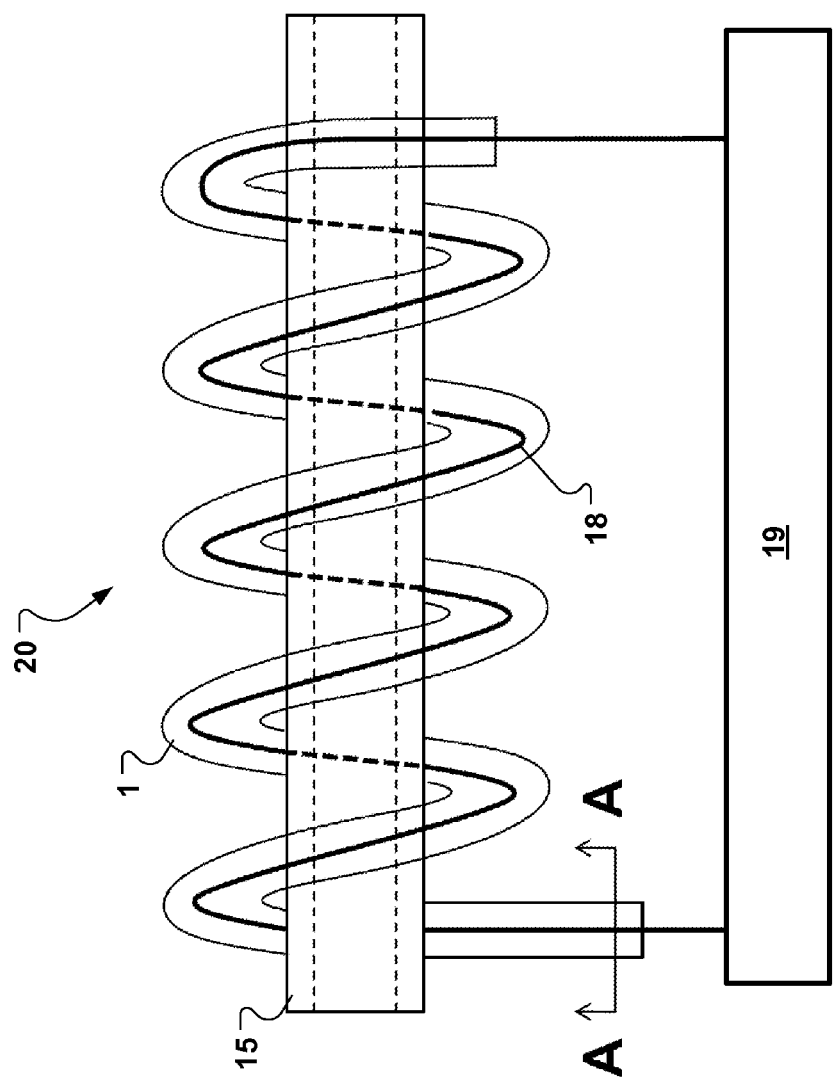
FIG. 11 is a side view of a wire coated with sorbent material and wrapped around a membrane.
Figure 12:
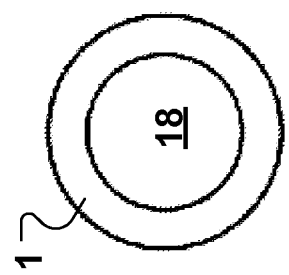
FIG. 12 is a cross-sectional view of the sorbent covered wire of FIG. 11.
Figure 13:
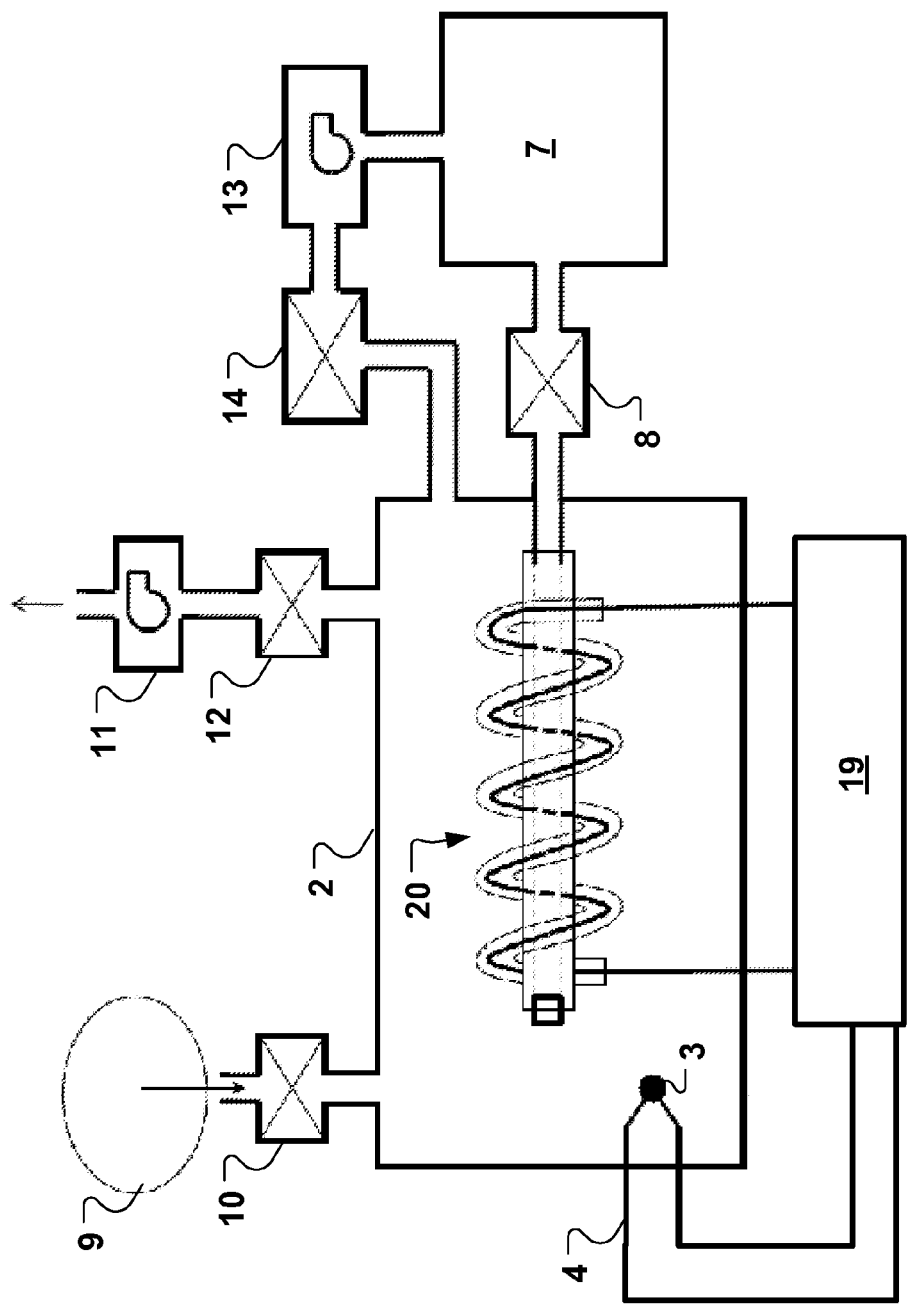

FIG. 11 illustrates an implementation in which the membrane (15), the sorbent material (1), and the temperature control element (18) occupy substantially the same volume. With further respect to FIG. 12, a portion of a length of the temperature control element (18) is coated with the sorbent material (1) as shown by Section A-A. The coated temperature control element (18) may then be wrapped around the tubular membrane (15) in an essentially concentric manner to form an inlet assembly (20) as shown in FIG. 13. The system illustrated in FIG. 13 may be operated, for example, using the techniques described above with respect to FIG. 4, FIG. 9, and/or FIG. 10.

In the example described above, near real time analysis may be achieved by directly heating sorbent material (1) since the thermal mass is significantly reduced when compared to an indirect heating method. Thus, the cycle time can also be reduced. Further, by directly heating sorbent material (1), the thermal efficiency is significantly increased. In addition, by evacuating housing (2) to a reduced pressure, conductive and convective thermal losses are reduced. Therefore, in some implementations, the pre-concentrator is able to operate with less power (average) than indirect heating techniques. Further, in some implementations, the membrane (15) of inlet assembly (20) is omitted, for example, to broaden the range of chemicals detected and/or the detection sensitivity of the system as described above.

Figure 14:
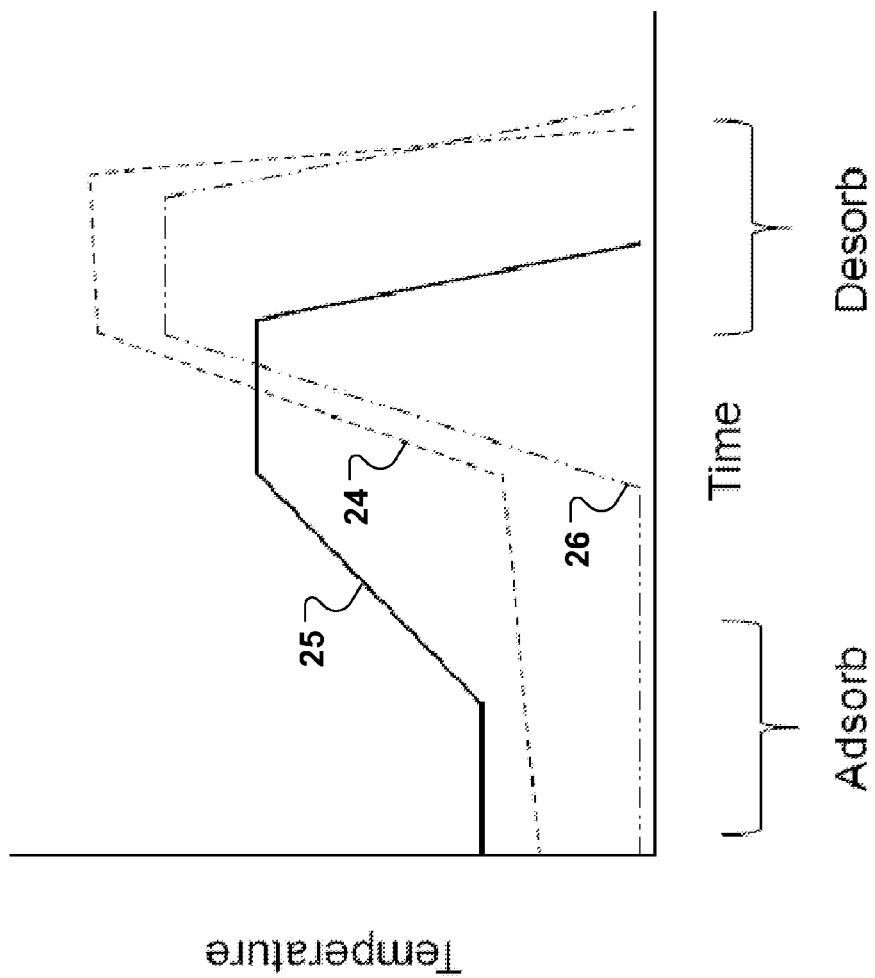
FIG. 14 is an exemplary temperature control profile.
Figure 15:
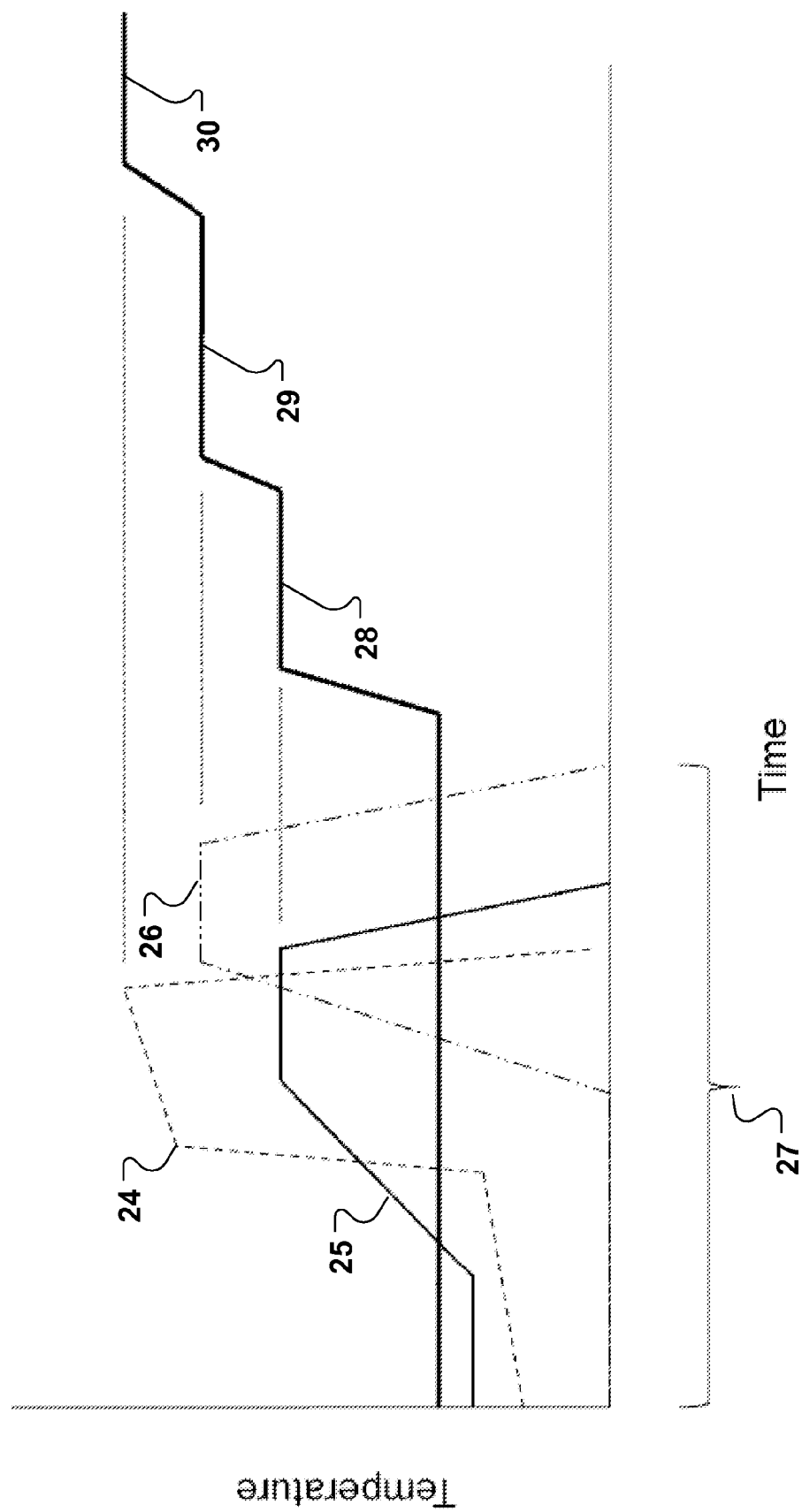
FIG. 15 is another exemplary temperature control profile.

In the descriptions of the systems and techniques of operating implementations and examples disclosed herein, it should be noted that the temperature applied to the sorbent material may be comprised of a temperature profile in which the temperature of the sorbent material is adjusted as a function of time rather than switched between two extremes. An effect of this method of operating is to further increase the pre-concentration gain of the pre-concentrator. FIG. 14 illustrates a graph of temperature versus time at which three candidate chemicals, chemical A (24), chemical B (25), and chemical C (26), substantially absorb or desorb from a particular choice of sorbent at different temperatures and over different lengths of time. As illustrated, each of the three candidate chemicals in this example desorbs from the sorbent material at different rates based on temperature. The different chemicals may be all of the same class (e.g., explosives) such that it is desirable to examine a limited number at one time in the chemical analyzer, or of different classes (e.g., CWAs and interferrents) such that it is desirable to exclude one or more chemicals from the chemical analyzer. FIG. 15 illustrates a graph showing how an intelligent temperature profile may be used to realize optimized performance from implementations of the pre-concentrator described herein. In this method of operating, the temperature is adjusted during the absorption time period (27) such that all chemicals of interest will be absorbed by the sorbent. The time period is chosen to yield a sufficient mass of absorbed material as described herein. After sufficient absorption, the temperature is adjusted during the desorption period (28) to a level that allows primarily chemical C to be desorbed into the mass spectrometer while retaining most of chemicals A and B. After chemical C is desorbed, the temperature is adjusted to a level during the desorption period (26), which primarily allows chemical B to be desorbed into the mass spectrometer while retaining most of chemical A. After this desorption period (26), the temperature is adjusted to a level during the desorption period (27), which allows chemical A to be desorbed into the mass spectrometer. These and other temperature control profiles may be implemented using temperature control units (6) and/or (19). It should be noted that the choices of materials, temperatures, and the number and type chemicals that are desirable to be absorbed and desorbed by the sorbent may be chosen to suit a particular application or implementation, and the particular choices disclosed herein are used only as examples.

Embodiments of the subject matter and the operations described in this specification can be implemented in digital electronic circuitry, or in computer software, firmware, or hardware, including the structures disclosed in this specification and their structural equivalents, or in combinations of one or more of them. Embodiments of the subject matter described in this specification can be implemented as one or more computer programs, e.g., one or more modules of computer program instructions, encoded on computer storage medium for execution by, or to control the operation of, temperature control units (6) and/or (19) and/or a pump and valve control system. Alternatively or in addition, the program instructions can be encoded on an artificially-generated propagated signal, e.g., a machine-generated electrical, optical, or electromagnetic signal, that is generated to encode information for transmission to suitable receiver apparatus for execution by temperature control units (6) and/or (19). A computer storage medium can be, or be included in, a computer-readable storage device, a computer-readable storage substrate, a random or serial access memory array or device, or a combination of one or more of them. Moreover, while a computer storage medium is not a propagated signal, a computer storage medium can be a source or destination of computer program instructions encoded in an artificially-generated propagated signal. The computer storage medium can also be, or be included in, one or more separate physical components or media (e.g., multiple CDs, disks, or other storage devices).

The terms "control unit" and "control system" (referred to herein generally as "controller") encompasses all kinds of apparatus, devices, and machines for performing the operations described in this specification, including by way of example a programmable processor, a computer, a system on a chip, or multiple ones, or combinations, of the foregoing The controller can include special purpose logic circuitry, e.g., an FPGA (field programmable gate array) or an ASIC (application-specific integrated circuit). The apparatus can also include, in addition to hardware, code that creates an execution environment for the computer program in question, e.g., code that constitutes processor firmware, a protocol stack, an operating system, a cross-platform runtime environment, a virtual machine, or a combination of one or more of them.

A computer program (also known as a program, software, software application, script, or code) can be written in any form of programming language, including compiled or interpreted languages, declarative or procedural languages, and it can be deployed in any form, including as a stand-alone program or as a module, component, subroutine, object, or other unit suitable for use in a computing environment. A computer program may, but need not, correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub-programs, or portions of code).

The processes and logic flows described in this specification can be performed by one or more programmable processors executing one or more computer programs to perform actions by operating on input data and generating output. The processes and logic flows can also be performed by, and apparatus can also be implemented as, special purpose logic circuitry, e.g., an FPGA (field programmable gate array) or an ASIC (application-specific integrated circuit).

Processors suitable for the execution of a computer program include, by way of example, both general and special purpose microprocessors, and any one or more processors of any kind of digital computer. Generally, a processor will receive instructions and data from a read-only memory or a random access memory or both. The essential elements of a computer are a processor for performing actions in accordance with instructions and one or more memory devices for storing instructions and data. Generally, a computer will also include, or be operatively coupled to receive data from or transfer data to, or both, one or more mass storage devices for storing data, e.g., magnetic, magneto-optical disks, or optical disks. However, a computer need not have such devices. Devices suitable for storing computer program instructions and data include all forms of non-volatile memory, media and memory devices, including by way of example semiconductor memory devices, e.g., EPROM, EEPROM, and flash memory devices; magnetic disks, e.g., internal hard disks or removable disks; magneto-optical disks; and CD-ROM and DVD-ROM disks. The processor and the memory can be supplemented by, or incorporated in, special purpose logic circuitry.

While this specification contains many specific implementation details, these should not be construed as limitations on the scope of any inventions or of what may be claimed, but rather as descriptions of features specific to particular embodiments of particular inventions. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. Moreover, the separation of various system components in the embodiments described above should not be understood as requiring such separation in all embodiments, and it should be understood that the described components and systems can generally be integrated together in a single product or packaged into multiple products.

The invention claimed is:

1. A chemical analysis system comprising:
a chemical analyzer;
a preconcentrator housing coupled to the chemical analyzer, the preconcentrator housing enclosing a heating element and a sorbent material, the heating element configured to heat the sorbent material to adsorb or desorb a chemical of interest;
a pump system coupled to the preconcentrator housing and the chemical analyzer, the pump system configured to evacuate the preconcentrator housing prior to desorption of the chemical of interest by reducing an internal pressure of the preconcentrator housing to a level substantially equal to an internal pressure of the chemical analyzer; and
a valve system coupled to the preconcentrator housing and configured to prevent any gas from entering into the evacuated preconcentrator housing during desorption of the chemical of interest and to maintain the internal pressure of the preconcentrator housing at the level substantially equal to the internal pressure of the chemical analyzer.

2. The chemical analysis system of claim 1, further comprising a temperature sensor enclosed in the preconcentrator housing, the temperature sensor having a temperature sense terminal to communicate a sensed temperature.

3. The chemical analysis system of claim 1, further comprising a temperature controller coupled to the heating element and configured to supply a current to the heating element.

4. A method of preconcentrating a sample, the method comprising:
providing a preconcentrator housing coupled to a chemical analyzer, the preconcentrator housing enclosing a heating element and a sorbent material, the heating element configured to heat the sorbent material to adsorb or desorb a chemical of interest;
providing a pump system coupled to the preconcentrator housing and the chemical analyzer, the pump system configured to evacuate the preconcentrator housing prior to desorption of the chemical of interest;
evacuating, using the pump system, the preconcentrator housing to reduce an internal pressure within the preconcentrator housing to a level substantially equal to an internal pressure of the chemical analyzer;
conducting current through the heating element to desorb the chemical of interest from the sorbent material into the evacuated preconcentrator housing; and
maintaining, by a valve system coupled to the preconcentrator housing, the internal pressure of the preconcentrator housing at the level substantially equal to the internal pressure of the chemical analyzer by preventing any gas from entering into the evacuated preconcentrator housing during desorption of the chemical of interest.

5. The method of claim 4, wherein conducting current through the heating element comprises controllably increasing a temperature of the heating element to increase a desorption rate of the chemical of interest.

6. The method of claim 4, further comprising sensing a temperature in the preconcentrator housing.

7. The method of claim 4, further comprising conducting current through the heating element to adsorb the chemical of interest.

* * * * *